(12) United States Patent  
Sanii et al.

(10) Patent No.: US 7,366,349 B2
(45) Date of Patent: Apr. 29, 2008

(54) TWO-DIMENSIONAL ARRAY SPECTROSCOPY METHOD AND APPARATUS

(75) Inventors: Babak Sanii, Davis, CA (US); David DiFrancesco, San Francisco, CA (US)

(73) Assignee: Pixar, Emeryville, CA (US)

( * ) Notice: Subject to any disclaimer, the term of this patent is extended or adjusted under 35 U.S.C. 154(b) by 737 days.

(21) Appl. No.: 10/980,617

(22) Filed: Nov. 2, 2004

(65) Prior Publication Data

US 2006/0092484 A1 May 4, 2006

(51) Int. Cl.
*G06K 9/00* (2006.01)

(52) U.S. Cl. ...................................... 382/165
(58) Field of Classification Search ................ 382/162, 382/167; 345/589–595; 358/504, 1.9, 518–520; 356/319, 326; 348/E17.004
See application file for complete search history.

(56) References Cited

U.S. PATENT DOCUMENTS

| | | |
|---|---|---|
| 3,220,792 A | 11/1965 | Vendig |
| 3,867,022 A | 2/1975 | Whatley et al. |
| 4,357,624 A | 11/1982 | Greenberg |
| 4,473,849 A | 9/1984 | Cool |
| 4,715,683 A | 12/1987 | Gregory et al. |
| 4,752,823 A | 6/1988 | Takashi et al. |
| 4,754,334 A | 6/1988 | Kriz et al. |
| 4,757,374 A | 7/1988 | Ramsay et al. |
| 4,827,434 A | 5/1989 | Hanau et al. |
| 4,958,220 A | 9/1990 | Alessi et al. |
| 4,979,032 A | 12/1990 | Alessi et al. |
| 4,985,762 A | 1/1991 | Smith |
| 5,206,918 A | 4/1993 | Levene |
| 5,234,414 A | 8/1993 | Hung |

(Continued)

FOREIGN PATENT DOCUMENTS

| | | |
|---|---|---|
| EP | 0 637 731 | 2/1995 |
| EP | 0 814 603 A2 | 12/1997 |
| WO | WO 95/31794 | 11/1995 |

OTHER PUBLICATIONS

Foley, et al.; "Achromatic and Colored Light," *Computer Graphics: Principles and Practice*; Second Edition, Chapter 13, (1990) pp. 563-604.

(Continued)

*Primary Examiner*—Jose L. Couso
(74) *Attorney, Agent, or Firm*—Townsend and Townsend and Crew LLP

(57) ABSTRACT

A spectroscope includes a light source providing a first and a second range of wavelengths, a dispersion unit to receive light and to output the first and second range of wavelengths at different angles, a positioning mechanism to position the dispersion unit such that the first range of wavelengths is applied to a first patch of a frame of film, to position the dispersion unit such that the second range of wavelengths is applied to the first patch but not the second patch and the first range of wavelengths is applied to the second patch at a second time, and to position the dispersion unit such that the second range of wavelengths is applied to the second patch, a first detector to detect responses from the frame of film from the first patch, and a second detector to independently detect responses from the frame of film from the second patch.

20 Claims, 8 Drawing Sheets

U.S. PATENT DOCUMENTS

| | | | |
|---|---|---|---|
| 5,272,518 | A | 12/1993 | Vincent |
| 5,528,339 | A | 6/1996 | Buhr et al. |
| 5,537,157 | A | 7/1996 | Washino et al. |
| 5,754,184 | A | 5/1998 | Ring et al. |
| 6,359,676 | B1 | 3/2002 | Treiber et al. |
| 6,895,110 | B2 * | 5/2005 | Rao .......................... 382/162 |
| 7,075,643 | B2 * | 7/2006 | Holub ....................... 356/326 |
| 2002/0063963 | A1 | 5/2002 | Whitehead et al. |

OTHER PUBLICATIONS

Gennetten, "RGB to CMYK Conversion Using 3-D Barycentric Interpolation," SPIE Conference on "Device-Independent Color Imaging and Imaging Systems Integration," (Feb. 1-3, 1993) San Jose, California, vol. 1909, pp. 116-126.

Gentile, et al.; "A Comparison of Techniques for Color Gamut Mismatch Compensation"; *Journal of Imaging Technology*; (Oct. 1990), vol. 16, No. 5; pp. 176-181.

Granger, "Achieving Device Independence in Color Through Appearance Modeling," SPIE Conference on "Device-Independent Color Imaging and Imaging systems Integration," (Feb. 1-3, 1993) San Jose, California; vol. 1909; pp. 15-18.

Guth, "Model for Color Vision and Light Adaptation," *Journal of the Optical Society of America*: vol.8, No. 6 (Jun. 1991) pp. 976-993.

Has, "Color Management—Current Approaches, Standards and Future Perspectives": Proceedings of IS&T's Eleventh International Congress on Advances in Non-Impact Printing Technologies, Hilton Head, South Carolina; pp. 441-445.

Has, et al.; "Color Management: Current Practice and the Adoption of a New Standard," *Advances in Printing Science and Technology*, vol. 23, pp. 51-58, (1997). (Conference proceedings of the International Association of Research Institutes for the Graphic Arts Industry, held in Paris, Sep. 1995).

Has, et al.; "Current Practice and the Adoption of a New Standard," Proceedings of the Commission Internationale de l'Eclairage (CIE), Expert Symposium on Colour Standards for Image Technology; (held in Vienna, Mar. 1996) Wien, CIE, (1998).

http://www.metalfilmcorp.com/pictures/april103/metalfsh.jpg, printed Jun. 23, 2003, 1 page.

Hunt, "Model of Color Vision for Predicting the Appearance of Colors Under Different Viewing Conditions"; SPIE Conference on "Device-Independent Color Imaging and Imaging systems Integration;" (Feb. 1-3, 1993) San Jose, California; vol. 1909, pp. 12-14.

Inoshiro, Kuro5hin, Kuro5hin.org Mission Statement, updated Sep. 10, 2000, http://www.kuro5hin.org/special/mission, printed Jul. 23, 2003, p. 1 of 2.

Kim et al., "Development of Color Management System Prototype," IEEE (1998) pp. 2539-2532.

MacDonald, "Developments in Colour Management Systems," Displays, vol. 16, No. 4, (1996) pp. 203-211.

Metafilmcorp.com, About Us, http://www.metafilmcorp.com/about.htm, printed Jun. 23, 2003, p. 1 of 1.

Metafilmcorp.com, Digital Intermediate, The totally digital post production process, http://www.metalfilmcorp.com/ei_overview.htm, printed Jun. 23, 2003, 2 pages.

Metafilmcorp.com, LCD technology, http://www.metafilmcorp.com/metaflash_technology.htm, printed Jun. 23, 2003, 2 pages.

Murch et al.; Apple Color Management System (ColorSync.TM.); SPIE Conference on "Device-Independent Color Imaging and Imaging systems Integration;" (Feb. 1-3, 1993) San Jose, California; vol. 1909, pp. 184-188.

Ramamurthy et al., "Achieving Color Match Between Scanner, Monitor, and Film: A Color Management Implementation for Feature Animation," SMPTE Journal, (Jun. 1999) pp. 363-373.

SIGGRAPH 2003, High-Dynamic-Range Display System, http://www.siggraph.org/s2003/conference/etech/hdr.html, printed Aug. 19, 2003, 2 pages.

SONY, Sony Global, Press Releases, Sony develops SXRD, a display device capable of generating high resolution, high contrast images of film quality smoothness, http://www.sony.net/SonyInfo/News/Press/200302/03-008E/printed Jun. 27, 2003, 3 pages.

Sunnybrook Technologies, HDR: Displaying the Real World, British Columbia, Canada, 2 pages.

Yourganov et al., Acquiring High Dynamic Range Video at Video Rates, Technical Report, Dept. of Computer Science, York University, May 2001, 17 pages.

* cited by examiner

TWO-DIMENSIONAL ARRAY SPECTROSCOPY METHOD AND APPARATUS

CROSS-REFERENCES TO RELATED APPLICATIONS

The present invention incorporates by reference for all purposes U.S. patent application Ser. No. 10/699,561 filed Oct. 30, 2003 now U.S. Pat. No. 6,895,110, and U.S. patent application Ser. No. 10/700,299, filed Oct. 31, 2003.

BACKGROUND OF THE INVENTION

The present invention relates to image to film transfer. More particularly, the present invention relates to techniques and apparatus for efficient recording of images to film media.

Throughout the years, movie makers have often tried to tell stories involving make-believe creatures, far away places, and fantastic things. To do so, they have often relied on animation techniques to bring the make-believe to "life." Two of the major paths in animation have traditionally included, drawing-based animation techniques and stop motion animation techniques.

Drawing-based animation techniques were refined in the twentieth century, by movie makers such as Walt Disney and used in movies such as "Snow White and the Seven Dwarfs" (1937) and "Fantasia" (1940). This animation technique typically required artists to hand-draw (or paint) animated images onto a transparent media or cels. After painting, each cel would then be captured or recorded onto film as one or more frames in a movie.

Stop motion-based animation techniques typically required the construction of miniature sets, props, and characters. The filmmakers would construct the sets, add props, and position the miniature characters in a pose. After the animator was happy with how everything was arranged, one or more frames of film would be taken of that specific arrangement. Stop motion animation techniques were developed by movie makers such as Willis O'Brien for movies such as "King Kong" (1933). Subsequently, these techniques were refined by animators such as Ray Harryhausen for movies including "Mighty Joe Young" (1948) and Clash Of The Titans (1981).

With the wide-spread availability of computers in the later part of the twentieth century, animators began to rely upon computers to assist in the animation process. This included using computers to facilitate drawing-based animation, for example, by painting images, by generating in-between images ("tweening"), and the like. This also included using computers to augment stop motion animation techniques. For example, physical models could be represented by virtual models in computer memory, and manipulated.

One of the pioneering companies in the computer-generated animation (CG animation) industry was Pixar. Pixar is more widely known as Pixar Animation Studios, the creators of animated features such as "Toy Story" (1995) and "Toy Story 2" (1999), "A Bugs Life" (1998), "Monsters, Inc." (2001), "Finding Nemo" (2003), "The Incredibles" (2004), and others. In addition to creating animated features, Pixar developed computing platforms specially designed for CG animation, and CG animation software now known as RenderMan®. By moving to CG animation, Pixar was faced with additional challenges.

One such challenge was how to accurately and effectively transfer CG animation images onto film, as discussed in the pending patent application discussed above. One specific aspect of this process has been how to correctly profile and/or calibrate a film transfer device, such as a laser film recorder, for a given film media or film stock.

Previous techniques for profiling and/or calibrating a film recorder have been used by Pixar. One such technique included first exposing multiple frames of film to different colors of light in the RGB color space in the film recorder. This included exposing each frame of film to a single unique RGB color. Next, once the film was developed, each frame of film was subjected to a spectroscopic analysis to determine a color in XYZ color space. One such method included determining the amount of light transmitted through each frame (i.e. color density) with respect to wavelength of light. Based upon this data, an RGB to XYZ color space mapping for the film recorder could be determined. In practice, this technique has been very time consuming.

As an example of this previous technique, four thousand frames of film were used and spectroscopicaly analyzed to profile a laser film recorder. Initially, a film recorder exposed each unexposed frame of film to a unique combination of {red, green, blue} values (RGB color space) from an available palette, such as frame 1 to {1,0,0}, frame 2 to {2,0,0}, frame 3 to {0,0,15}, ... frame 4000 to {128, 128, 255}. The inventors of the present invention have noted that the process of recording about four thousand frames of film, although semi-automated, took hours to complete.

Next, each frame was developed and each frame was subjected to a spectroscopic analysis to determine the intensity of light transmitted at different wavelengths of light (XYZ color space). For example, frame 1 was exposed to white light and a portion of that light was transmitted through frame 1. The transmitted light was then projected through a spectral analyzer. In one system, the spectral analyzer included a prism that would disperse the transmitted light into a rainbow pattern. Additionally, the prism was rotatable such that only a specific portion of the rainbow pattern would strike a camera at a time. Accordingly, the system could detect transmissions of frame 1 with respect to wavelength. The inventors of the present invention have noted that the process of scanning four thousand frames of film, again semi-automated, took hours to complete.

Next, based upon the transmissions per wavelength per frame, a profile for the film recorder was determined. In the above-mentioned patent application, this process was described and termed "determining an RGB to XYZ color space mapping" for the film/film recorder.

In practice, the previous technique has been too time consuming to perform regularly. The inventors of the present invention desire to perform the calibration process more frequently than was done before. For example, calibrating a film recorder every week, every day, after filming out one copy of a feature, receiving a new stock of film media, or the like. To have this ability, the calibration time must be dramatically decreased. In the example above, over 1 day was required to profile the film scanner, which would be too long.

The inventors have considered applying technology from the desktop paper scanner/slide scanner market towards the present problem. For example, for a slide or transparency scanner, a light source provides a white light illumination to a target (e.g. slide, transparency), and three or more CCDs on the back side of the target capture the transmissions through the target. The three or more CCDs typically have filters on top of them such as a red, green, or blue gels at specific frequencies. For example, the red filter may peak at 680 nm+−10 nm, the green may peak at 550+−10 nm, and the like. Such systems are typically single light-pass systems.

In another configuration, a light source provides white light, but a red, green, or blue gel is placed between the white light and the target. Accordingly, a red, green, or blue color is applied to the target, and a monochrome CCD detects the transmission. In this configuration, the filters are similar to the above. Using these technologies, transmissions through the target are captured only about the peak RGB frequencies. Such systems are typically three light-pass systems.

Drawbacks to these approaches include that these scanners cannot provide spectroscopic analysis, because only three distinct frequencies of light are sampled. To perform a spectroscopic analysis, the wavelengths of light illuminating the film should be continuous over the spectrum. An example of the drawback is if a first slide has a reddish color density color peak at 680 nm, and if a second slide has a higher density reddish color peak at 700 nm. Using the slide scanner techniques, the first slide would have a bright recorded intensity because the color of the red filter (680+−10 nm) matches the color (680 nm) of the first slide. However, the second slide would have a lower recorded intensity because the color of the red filter (680+−10 nm) does not match the color (700 nm) of the second slide. In contrast, using a spectroscope, the second slide would have higher intensity, because the second slide has a higher density. Because of the narrow range of filters applied with conventional scanners, the densities of the film are not correctly measured. Accordingly, the inventors do not believe that conventional slide or transparency technologies are relevant for the present application.

In light of the above, what is required are methods and apparatus to more quickly and efficiently profile and calibrate a film recorder without the drawbacks discussed above.

BRIEF SUMMARY OF THE INVENTION

The present invention relates to digital image transfer to tangible media. More particularly, the present method relates to apparatus and techniques for increasing digital image to film media transfer speed quality.

According to one aspect of the invention, a method for calibrating a film transfer device and film media combinations disclosed. One technique includes providing a frame of film media including a plurality of patches including a first patch, and a second patch, wherein the first patch is exposed to a first RGB color combination, and wherein the second patch is exposed to a second RGB color combination, providing an illumination source configured to output a beam of light, and separating the beam of light into a beam of light at approximately a first wavelength and into a beam of light at approximately a second wavelength. Various techniques also include illuminating the first patch with the beam of light at approximately the first wavelength, determining first transmissions from the first patch in response to the beam of light at approximately the first wavelength, thereafter substantially simultaneously illuminating the first patch with the beam of light at approximately the second wavelength and illuminating the second patch with the beam of light at approximately the first wavelength, and substantially simultaneously determining second transmissions from the first patch in response to the beam of light at approximately the second wavelength, and determining first transmissions from the second patch in response to the beam of light at approximately the first wavelength. Processes may also include illuminating the second patch with the beam of light at approximately the second wavelength, determining second transmissions from the second patch in response to the beam of light at approximately the second wavelength, thereafter determining an XYZ color space representation of the first transmissions and the second transmissions for the first patch, and determining an XYZ color space representation of the first transmissions and the second transmissions for the second patch.

According to another aspect of the invention, a two-dimensional spectroscope is disclosed. One apparatus includes a radiation source configured to provide radiation at a plurality of wavelengths including a first range of wavelengths and a second range of wavelengths, and a dispersion unit coupled to the radiation source configured to receive the radiation and configured to output the first range of wavelengths angularly displaced from the second range of wavelengths. Various apparatus may also include a positioning mechanism coupled to the dispersion unit, the radiation source or a frame of film. In specific embodiments, the positioning mechanism is configured to position the dispersion unit such that the first range of wavelengths is applied to a first patch of a frame of film but not a second patch of the frame of film at a first time, configured to position the dispersion unit such that the second range of wavelengths is applied to the first patch but not the second patch and the first range of wavelengths is applied to the second patch at a second time, and configured to position the dispersion unit such that the second range of wavelengths is applied to the second patch but not the first patch at a third time, and a plurality of detectors comprising a first detector and a second detector, wherein the first detector is configured to detect responses from the frame of film from the first patch, and wherein the second detector is independently configured to detect responses from the frame of film from the second patch.

According to yet another aspect of the invention another technique is disclosed. Various techniques include illuminating each of a plurality of patches on a frame of media with unique portions of a spectrum, wherein a first portion of the spectrum illuminates a first patch, wherein a second portion of the spectrum illuminates a second patch, and wherein each of the plurality of patches on the frame of media are prerecorded with unique RGB values, and determining a first amount of responses for each of the plurality of patches on the frame of media in response to the unique portions of the spectrum. A process may also include repositioning the spectrum relative to the frame of media, illuminating each of the plurality of patches on the frame of media with other unique portions of the spectrum, wherein a second portion of the spectrum illuminates the first patch, and wherein a third portion of the spectrum illuminates the second patch, determining a second amount of responses for each of the plurality of patches on the frame of media in response to the other unique portions of the spectrum, and determining an RGB to XYZ color space representation associated with the frame of media in response to the first amount of responses, the second amount of responses, and to the unique RGB values.

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which.

DETAILED DESCRIPTION OF THE INVENTION

Figure 1:
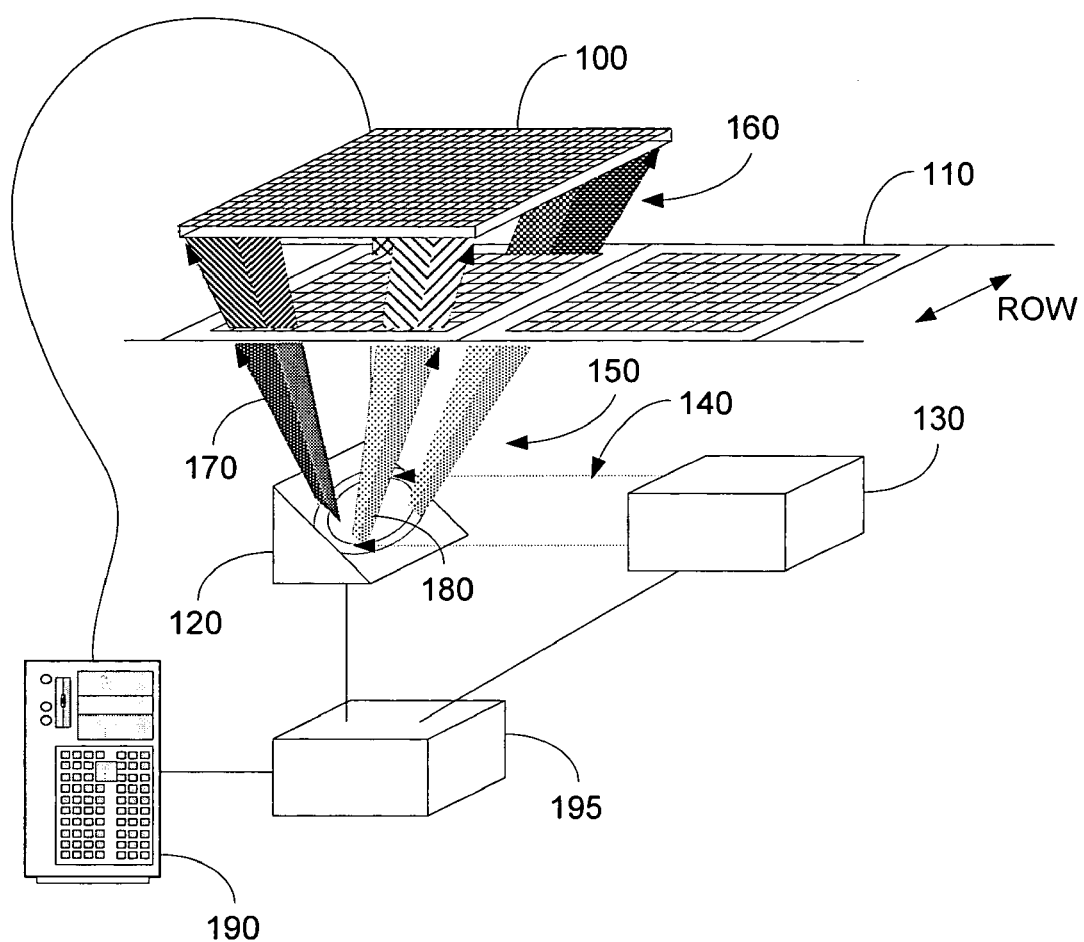
FIG. 1 illustrates an embodiment of the present invention.

FIG. 1 illustrates an embodiment of the present invention. FIG. 1 includes a CCD array (sensing unit) 100, a sample media 110, a prism 120, and a light source 130.

In FIG. 1, light source 130 provides a beam of light 140 to prism 120. In embodiments of the present invention, beam of light 140 typically includes light at a number of wavelengths. In one embodiment, where light 140 is a white light, the wavelength of light is mostly continuous across the spectrum and the light is approximately uniform in intensity at the different wavelengths. In embodiments, the wavelength of light includes wavelengths from approximately 380 nanometers to approximately 750 nanometers; from approximately 400 nm to approximately 700 nm, and the like.

In embodiments of the present invention, the intensities of light at different wavelengths may be non-uniform for light 140. For example, if the intensity of light near 680 mm is higher than the intensity of light near 400 nm, light source 130 would appear reddish in color.

In other embodiments of the present invention, the wavelength of light may be continuous across the whole spectrum or only across a portion of the spectrum. For example, a spectrum of light source 130 may range from about 550 mm to approximately 700 nm; may range from 400 nm to 500 nm; may range from 400 mm to 500 m and from 600 m to 700 mm, and the like.

In other embodiments, light source 130 may include one or more colored light sources, such as colored light emitting diodes (LEDs), or the like. In such embodiments, the wavelength of light 140 should also be mostly continuous across at least a portion of the spectrum.

As illustrated in FIG. 1, as light 140 passes through prism 120, light 140 is dispersed into a "rainbow pattern" 150. In this embodiment, rainbow pattern 150 is typically continuous across at least a part of the spectrum and represents the wavelengths of light making-up light 140.

In FIG. 1, the rainbow pattern 150 is directed towards the sampling media 110, as shown. In various embodiments, sampling media 110 may be a translucent/transparent media, such as exposed and developed film, and the like. In other embodiments, sampling media 110 may be reflective and/or opaque media, such as photographic paper, printed media, film, or the like. In such embodiments, light source 130 and CCD array 100 are typically positioned on the same side of sampling media 110.

In some embodiments of the present invention, sampling media 110 is a frame of film media that is divided into a number of patches. For example, in some embodiments, the number of patches are on the order of 1,000 patches, and in other embodiments, the number of patches are on the order of 4,000 patches. In other embodiments, the number of patches may vary according to engineering requirement, for example, the number may range from approximately 100 patches to 10,000 patches, or more.

In the present embodiments, each of the patches on sampling media 110 corresponds to a location on sampling media 110 that was exposed to a combination of red, green, and blue values (RGB). In some embodiments, each patch on sampling media 110 is exposed to a unique combination of RGB values, and in other embodiments, some patches on sampling media 110 may be exposed to the same RGB values.

In some embodiments, the RGB values applied to the patches are approximately the same as was applied to entire frames of film in the patent application incorporated above. For example, as was discussed, a unique RGB value to each of a thousand frames of film in order to characterize the film recorder. In the present embodiment, as opposed to recording a thousand frames of film with a single and unique RGB value, each frame in the present embodiment may be recorded with a thousand (or more) RGB values. As referred to above, one or more frames may include approximately 90, 300, 1,000, 2,000, 4,000, or the like patches that record different RGB values, or the like.

In the present embodiments, as can be seen, different portions of rainbow pattern 150 are exposed to different portions of sampling media 110 at one time. For instance, the red portion 170 of rainbow pattern 150 is directed towards the left portion of sampling media 110 at the same time the blue portion 180 of rainbow pattern 150 is directed towards the right portion of sampling media 110. Because the patches are distributed about sampling media 110, different patches of sampling media 110 are exposed to different portions of rainbow pattern 150 at the same time. In some embodiments, some patches of (e.g. along a CCD row) sampling media 110 are exposed to the same portion of rainbow pattern 150 at the same time.

In FIG. 1, as each patch on sampling media 110 is exposed to a portion of rainbow pattern 150, each patch transmits a measurable amount of light 160. Light 160 is then captured by one or more CCDs from CCD array 100. In embodiments of the present invention, CCD array 100 is typically a "black and white" or grayscale CCD sensor array. In the present embodiment, the correspondence between CCDs and patch may be determined before or after rainbow pattern 150 illuminates sampling media 110. The data from CCD array 100 is then input into a computing unit 190.

In embodiments of the present invention, the sensing unit may be an area scan, a line scan camera, a CCD camera for spectroscopy, or the like, such as available from Dalsa Corporation, Roper Scientific Photometrics, Princeton Instruments, Pixis, and the like. In other embodiments, the sensing unit may be a CMOS device, an array of independent light detectors, or the like.

As described in the above-referenced patent application, computing unit 190 performs one or more calculations to convert the data from the CCD array into a color in the XYZ space, and to determine an RGB to XYZ color space mapping for a recorder device. In embodiments of the present invention, the recorder device is a film recorder that recorded the RGB values onto sampling media 110.

In the present embodiment, computing unit 190 is also configured to adjust the position of prism 120 relative to light source 130 as a function of time. As will be illustrated below, in embodiments of the present invention, prism 120 is rotated relative to light source 130 such that rainbow pattern 150 "sweeps" across the entire face of sampling media 110. By doing this, typically each patch from sampling media 110 is exposed to the entire spectrum of rainbow pattern 150 as a function of time. In various embodiment, a positioning unit 195 may be used to adjust the position of prism 120 relative to light source 130.

In the present embodiments, it is contemplated that the wavelengths of rainbow pattern 150 is substantially continuous, so that as prism 120 is rotated, each patch is exposed to a number of different wavelengths. In embodiments of the present invention, rainbow pattern 150 typically has a wavelength range from about 380 nm to about 750 nm, although a greater or smaller range is clearly contemplated.

In embodiments of the present invention, the amount of light 160 associated with each patch is a function of time, and a function of the portion of rainbow pattern 150 that strikes each patch. In one embodiment, to simplify the computations, instead of measuring the amount of light 160 for each wavelength, the amount of light 160 is measured per "bucket" of wavelengths. For example, in some examples, buckets of wavelengths are defined to be from approximately 3 to 6 nm wide, from approximately 4 to 5 nm wide, approximately 4.5 nm wide, or the like. In a case where the wavelengths for rainbow pattern 150 range from 380 nm to 750 nm and buckets are 4.5 nm apart, approximately 82 buckets of wavelengths are defined. Accordingly, in this example, the amount of light 160 is measured by CCD array 100 eighty-two distinct times for each patch on sampling media 110, once in response to each bucket of wavelengths.

In embodiments of the present invention, positioning unit 195 may be a galvanometer, a stepper motor, or the like. In other embodiments, the film could move, or the film and the CCD could move, or the like.

Figure 2A:
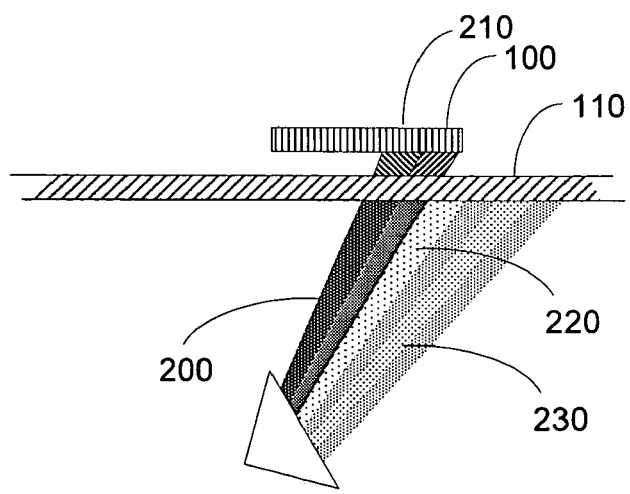
FIGS. 2A-F illustrate embodiments of the present invention.

FIGS. 2A-F illustrate embodiments of the present invention. In FIG. 2A, prism 120 is rotated relative to light source 130, such that red bucket 200 is exposed to a first patch 210 on sampling media 110, a yellow bucket 220 and blue bucket 230 falls outside sampling media 110.

Figure 2B:
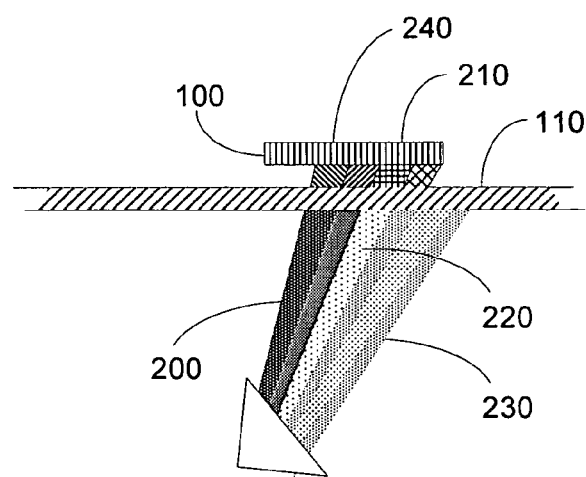

In FIG. 2B, as seen, prism 120 is rotated relative to light source 130, such that red bucket 200 is exposed to a second patch 240 on sampling media 110, yellow bucket 220 is exposed to first patch 210, and blue bucket 230 falls outside sampling media 110.

Figure 2C:
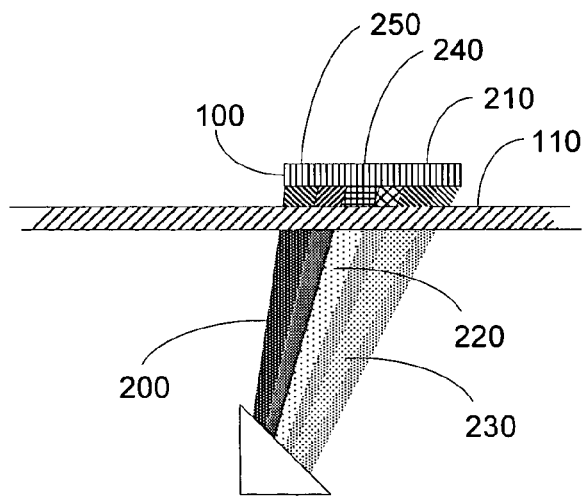

In FIG. 2C, as seen, prism 120 is rotated relative to light source 130, such that red bucket 200 is exposed to a third patch 250 on sampling media 110, yellow bucket 220 is exposed to second patch 240, and blue bucket 230 is exposed to first patch 210.

Figure 2D:
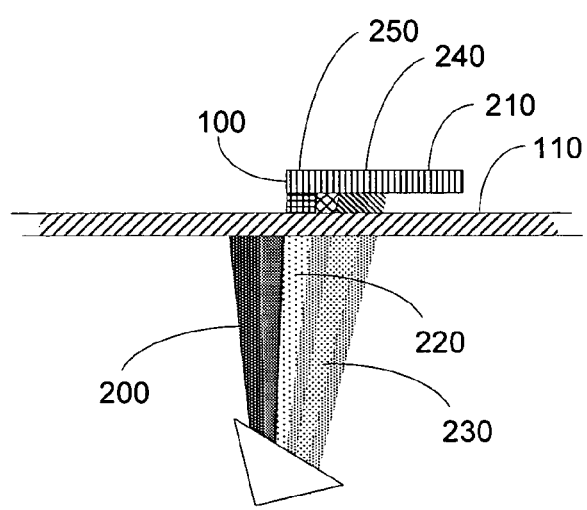

In FIG. 2D, as seen, prism 120 is rotated relative to light source 130, such that red bucket 200 falls outside sampling media 110, yellow bucket 220 is exposed to third patch 250, and blue bucket 230 is exposed to second patch 240.

Figure 2E:
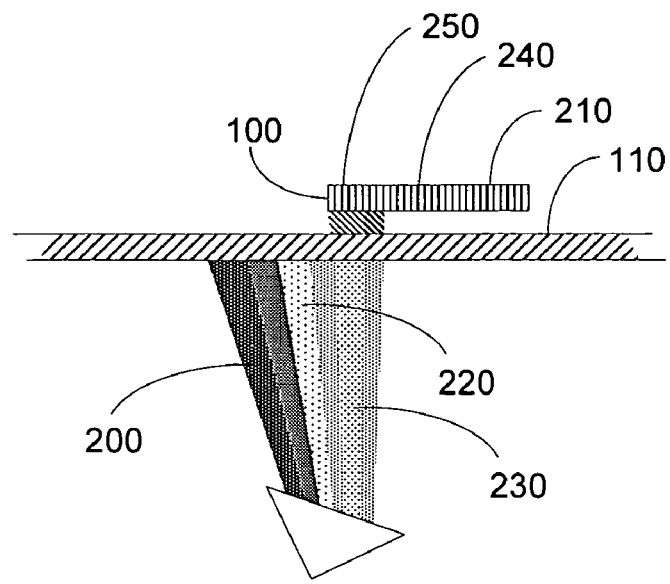

In FIG. 2E, as seen, prism 120 is rotated relative to light source 130, such that red bucket 200 and yellow bucket 220 fall outside sampling media 110, and blue bucket 230 is exposed to third patch 250.

As can be seen above, the patches above are illuminated by different buckets of wavelengths in time.

Figure 2F:
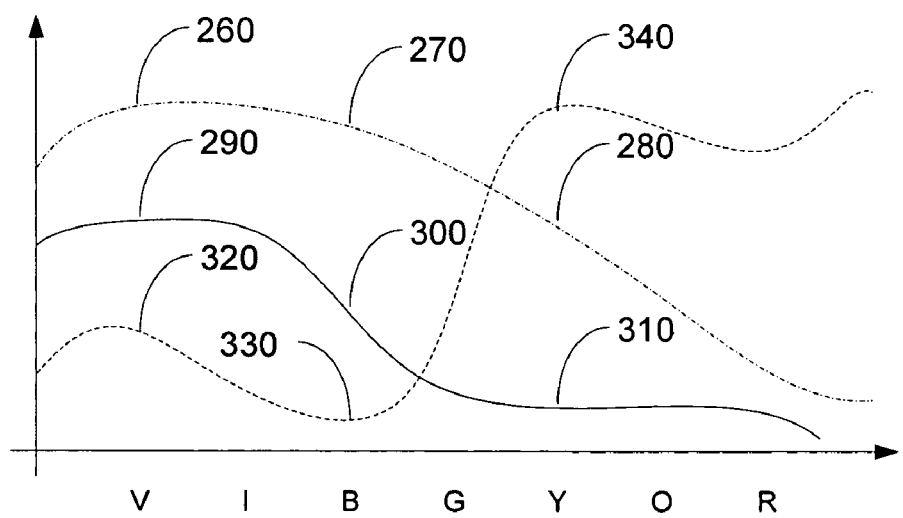

FIG. 2F illustrates a plot of transmissions of the above patches with respect to the three buckets of wavelengths. From, FIG. 2A, first patch 210 transmits light 260; FIG. 2B, first patch 210 transmits light 270; and FIG. 2C, first patch 210 transmits light 280. Additionally, from in FIG. 2B, second patch 240 transmits light 290; FIG. 2C, second patch 240 transmits light 300; and FIG. 2D, second patch 240 transmits light 310. Further, From FIG. 2C, third patch 250 transmits light 320; FIG. 2D, third patch 250 transmits light 330; and FIG. 2E, third patch 250 transmits light 340. As can be seen in the plot in FIG. 2F, the response for each patch as a function of wavelength bucket is determined.

Figure 3A:
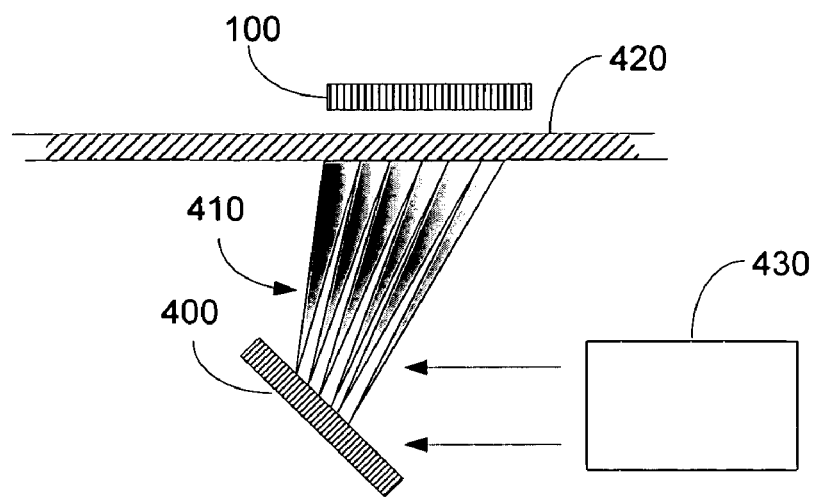
FIGS. 3A-B illustrate additional embodiments of the present invention.
Figure 3B:
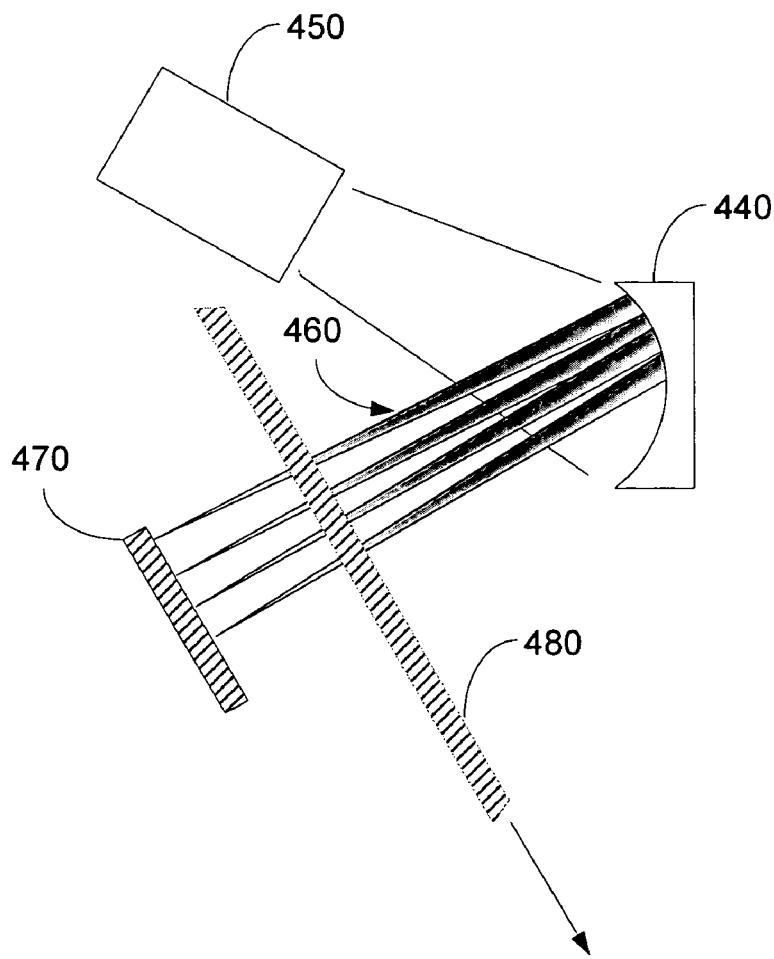

FIGS. 3A-B illustrate additional embodiments of the present invention. More specifically, FIG. 3A illustrates an embodiment including a grating 400. In contrast to the embodiment in FIG. 1, using grating 400, provides a greater number of rainbow patterns 410 that illuminate sampling media 420. Accordingly, to sweep the spectrum of rainbow patterns 410 across each patch of sampling media 420 requires a smaller angular motion of grating 400 relative to a light source 430. As is known, by changing parameters of grating 400, such as the grating spacing, different characteristics for rainbow patterns 410 may be achieved.

The embodiment in FIG. 3B illustrates use of a holographic prism 440. In this embodiment, a light 450 shines on holographic prism 440 and in turn a rainbow pattern 460 is produced. An array of CCD elements 470 is positioned at the focal plane of holographic prism 440. In operation, a sampling media 480 is passed across rainbow pattern 460, and the light transmissions of patches on sampling media 480 at different light frequencies are then recorded by CCD elements 470

Figure 4:
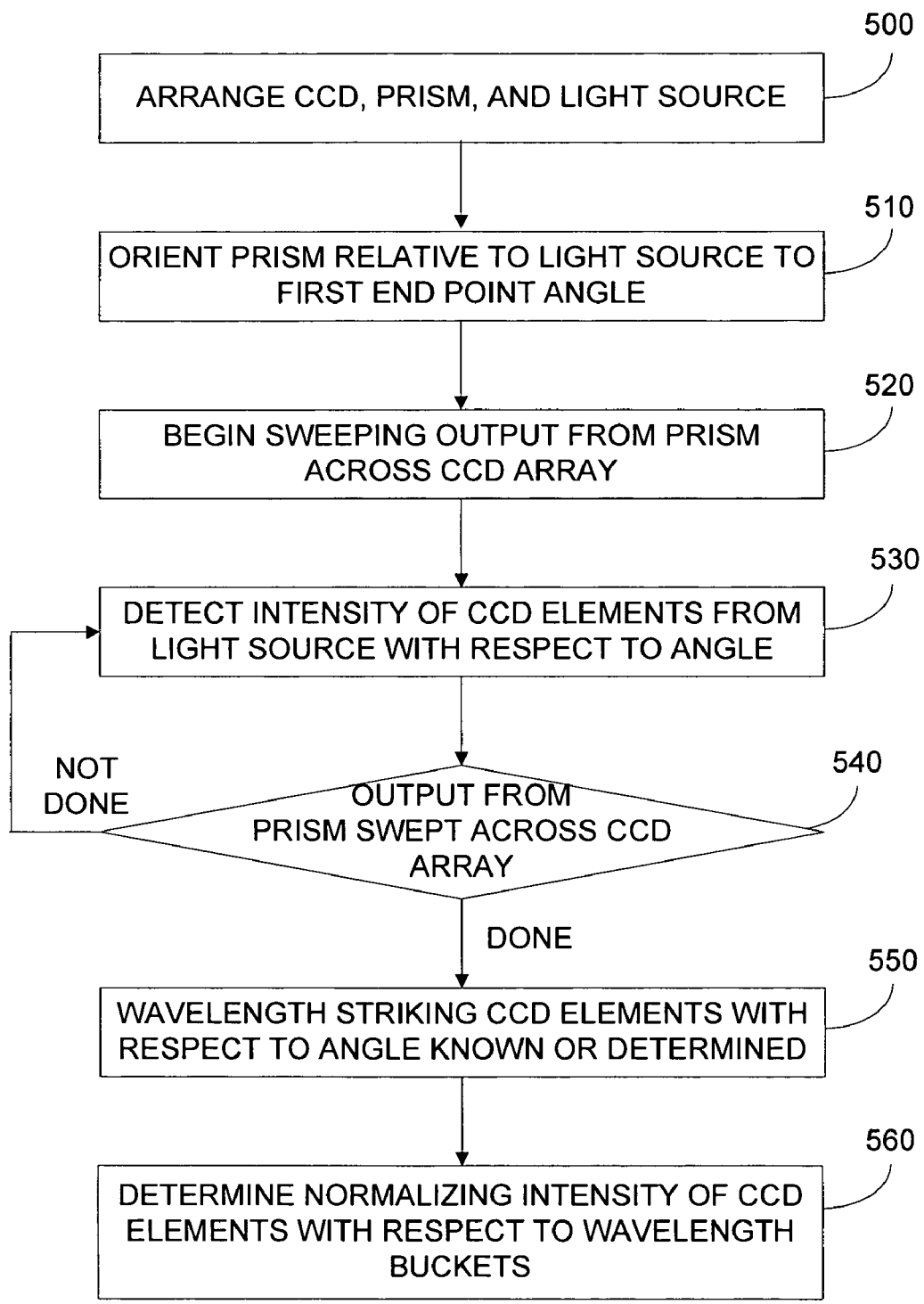
FIG. 4 illustrates a block diagram according to an embodiment of the present invention.

FIG. 4 illustrates a block diagram according to an embodiment of the present invention. More specifically, FIG. 4 illustrates a flow diagram with reference to the embodiment of FIG. 1, only for sake of convenience.

Initially, the embodiment shown in FIG. 1 is assembled, without sampling media 420, step 500. More specifically, CCD 100 is positioned behind where sampling media 420 is to be positioned. Next, computing unit 190 directs positioning unit 195 to position prism 150 relative to light source 130 at a movement "end point," step 510 In embodiments of the present invention, the movement end point is a position where rainbow pattern 150 falls-off where sampling media will be placed.

Computing unit 190 then directs positioning unit 195 to begin moving prism 150 relative to light source 130 to another movement "end point," step 520. In embodiments of the present invention, the other movement end point is also a position where rainbow pattern 150 falls-off where sampling media will be placed. In the present embodiment, while rainbow pattern 150 is sweeping across CCD 100, the intensities of the light detected by the CCDs is recorded as a function of position (e.g. angle or time), step 530, until the other "end point" is reached, step 560.

In embodiments of the present invention, a user knows beforehand how rainbow pattern 150 will be positioned based upon the position (e.g. angle or time) of prism 150 relative to light source 130, step 540. As a hypothetical example, a user knows that to sweep rainbow pattern 150 across sampling media 420, prism 150 should be positioned from 15.5 degrees to 25.6 degrees. Further, the user can determine where each wavelength bucket will strike CCD as a function of angle. As an example, the user can determine that a bucket of wavelengths about 550 nm is represented as a line positioned approximately on row numbers 100 and 101 of CCD 100 when prism 150 is positioned at 20.5 degrees.

In the present embodiment, based upon the knowledge of where each wavelength bucket will strike the CCD as a function of position (e.g. angle or time) (step 540), and the CCD readings as a function of position (e.g. angle or time) (step 530), the user correlates the intensities of the light detected by the CCDs with respect to wavelength buckets, step 550. In the present embodiment, the above steps are used to determine calibration data for light source 130 used in subsequent steps. For example, if light source 130 is yellowish, the intensities for yellow are higher than for blue or red. Accordingly, when determining transmissions of light from sampling media 420, the density calculations, should take into account that the applied yellow was more intense than other colors.

Figure 5:
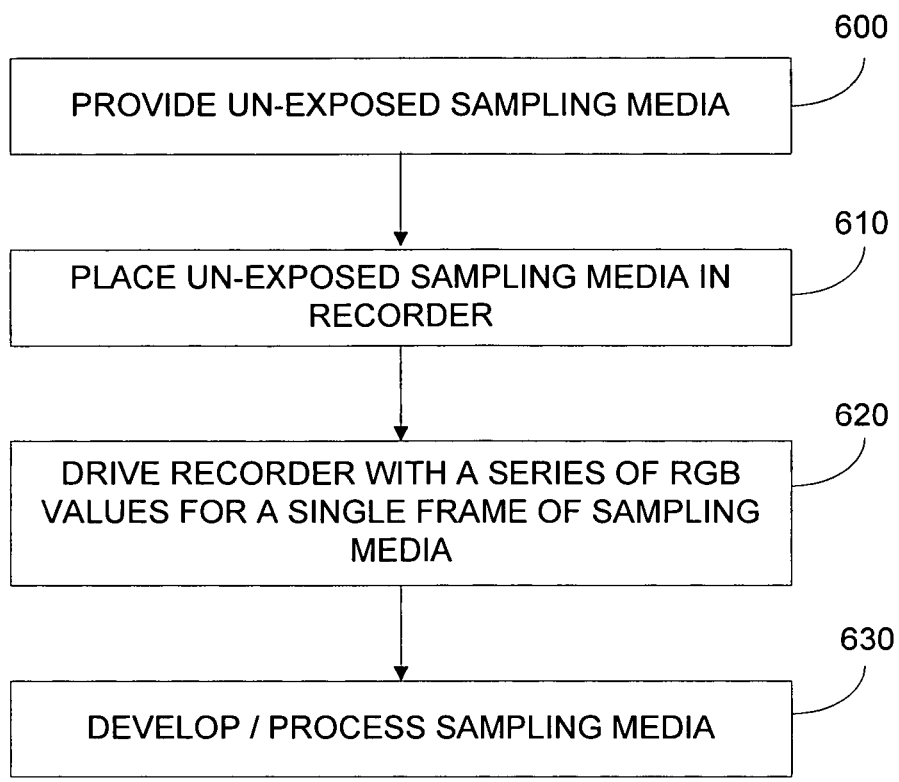
FIG. 5 illustrates a block diagram according to an embodiment of the present invention.

FIG. 5 illustrates a block diagram according to an embodiment of the present invention. More specifically, FIG. 5 illustrates a process for forming sampling media 420.

Initially, one or more frames of unexposed film media are provided, step 600. In embodiments of the present invention, the film media may be any conventional film media, such as "camera negatives," "intermediate stock," photographic negatives, photographic slides, or the like.

Next, the frames of un-exposed film are placed within a film recorder the user wishes to profile, step 610. The film recorder is then driven with more than one RGB patch values for each frame, step 620. In embodiments of the present invention, each patch in a frame is driven with a different RGB value, as discussed above. For example, one patch is exposed to RGB values of {200,200, 100}, another patch of the same frame is exposed to RGB values of {0,0,100}, and the like.

In embodiments of the present invention, the patches are arranged in a two-dimensional grid-type pattern on each frame of film. In other embodiments, many other two-dimensional positions for patches are contemplated, such as a running-brick pattern, hexagonal pattern, spots, or the like.

As discussed above, in various embodiments of the present invention a frame may have from approximately 1,000 to 4,000 patches. In other embodiments, a frame may have from approximately 100 to 10,000 patches, or more. In various implementations, the RGB values written to each patch may be unique. In another implementation, the same RGB values may be written to different patches in the same frame. Such an embodiment would allow the user to determine if the film recorder or the film media recorded colors non-uniformly (i.e. determine "flatness") across the frame. Further, in embodiments of the present invention, multiple frames of film may be recorded with the same RGB values so that more than one frame may be used for the calibration process. As an example, depending upon the number of patches per frame, and the number of RGB patch combinations, the number of frames may vary from 1 to 5, or more. In the present embodiment, the exposed film is then processed, step 630.

Figure 6A:
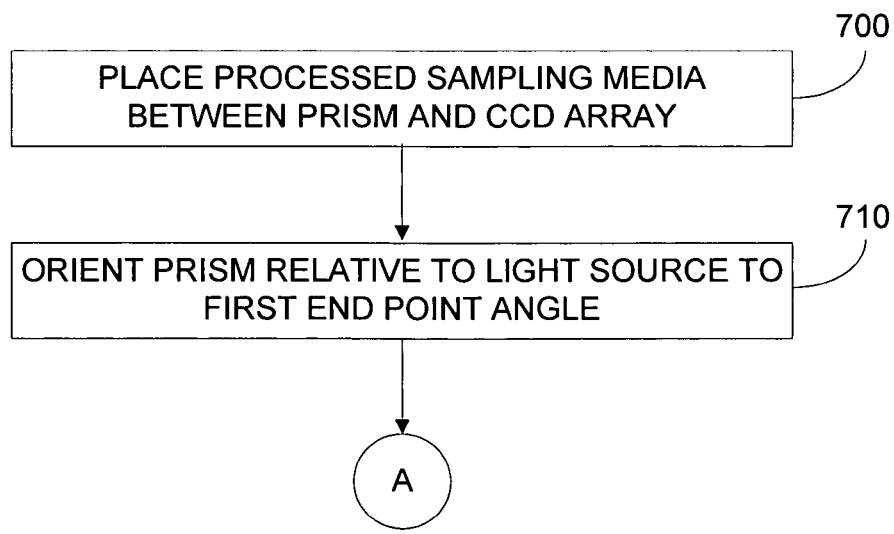
FIGS. 6A-C illustrates a block diagram according to an embodiment of the present invention.
Figure 6B:
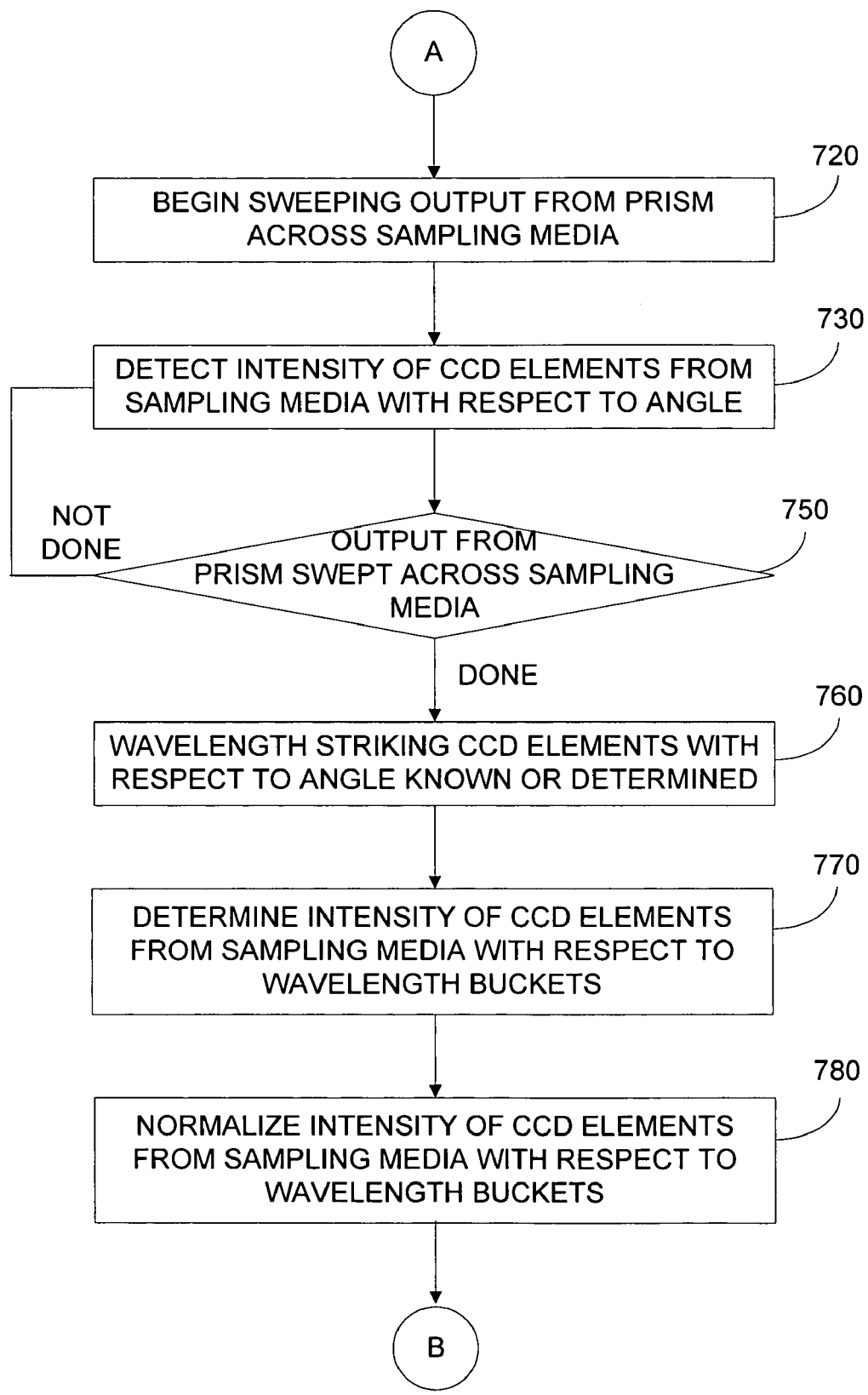
Figure 6C:
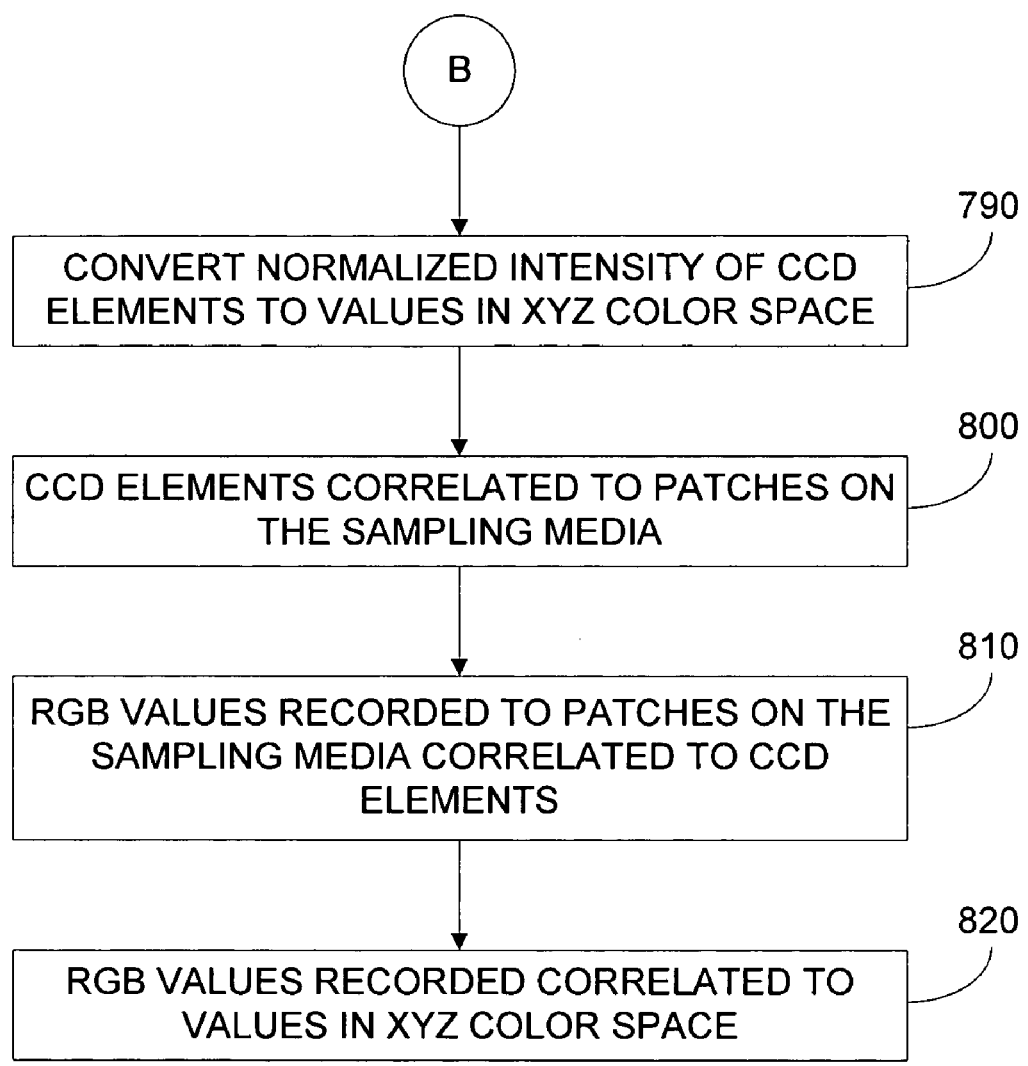

FIGS. 6A-C illustrate a block diagram according to an embodiment of the present invention. More specifically, FIGS. 6A-C illustrate a process for performing a two-dimensional spectroscopic analysis on sampling media 420.

Initially, the frame of developed film in FIG. 5 is provided between CCD 100 and prism 120, step 700. Next, computing unit 190 directs positioning unit 195 to position prism 150 relative to light source 130 at the movement "end point," step 710 In embodiments of the present invention, the movement end-point may be the same one described in step 510, above.

Next, computing unit 190 then directs positioning unit 195 to begin moving prism 150 relative to light source 130 to the other movement "end point," described above, step 720. In the present embodiment, while rainbow pattern 150 is sweeping across the frame of film, the intensities of the light transmitted through the patches of the frame are detected by the CCDs are recorded as a function of position (e.g. angle or time), step 730. This continues, until the other "end point" is reached, step 750.

In the present embodiment, based upon the knowledge of where each wavelength bucket will strike the CCD as a function of position (e.g. angle or time) (step 540), and the CCD readings for the frame of film as a function of position (e.g. angle or time) (step 730), the user correlates the intensities of the light through the frame of film detected by the CCDs with respect to wavelength buckets, step 760.

In FIGS. 6A-C, the intensity of light through the frame of film with respect to wavelength bucket is then normalized in view of the intensity of light from light source 130 with respect to wavelength bucket determined in step 550, above, for each pixel in the CCD, step 770. As a result, the spectroscopic readings are normalized. In embodiments of the present invention, the spectroscopic readings may be converted to an independent color space such as XYZ, for each pixel in the CCD, as was discussed in the above-mentioned patent application, step 780.

In the present embodiment, the locations of the CCD are then correlated to the locations of the patches on the film media, step 790. As an example, pixels A, B, C, and D of the CCD are mapped to a first patch, pixels E, F, G, and H of the CCD are mapped to a second patch, and the like. Any convention technique may be used to do this. Next, because the RGB values for each patch is known, RGB values may be associated with each pixel on the CCD, step 800.

Finally, an RGB to XYZ mapping can be determined based upon the XYZ value determined for each pixel (step 780), and the RGB value determined for each pixel (step 800), step 810.

In the foregoing specification, the invention has been described with reference to specific exemplary embodiments thereof. Many changes or modifications are readily envisioned. For example, in light of the above disclosure, one of ordinary skill in the art would recognize that positioning unit 195 could be adapted to move the film relative to prism 20. In other examples, other types of image to film transfer devices besides a laser film recorder can be profiled. For example, the film recorder may include a display, such as an LCD display, CRT display, microdisplay, DLP, or other type of display technology. The film is then exposed from light (LED, strobe, etc.) passing through or emanating from the display or from light reflected from the display. For example, technologies described in co-pending patent application incorporated by reference above may be adapted for use in the present embodiments.

In embodiments disclosed above illustrate using light transmissions to determine characteristics of the film, including film density, film density and color content, and the like. In other embodiments, reflective configurations are also contemplated. For example, a CCD may be positioned on the same side of the sampling media and receive reflections of light at different wavelengths from the sampling media. In other embodiments, a combination of optics may be used to focus the light source onto the prism or diffraction grating, holographic prism, and/or between the prism or diffraction grating to the frame of film media, and/or between the film media and the CCD array. In other embodiments, the system may also be configured to determine flatness or sharpness response of the film media.

In still other embodiments, the light source need not be a white light source. For example, light sources commonly used by conventional projectors may be used. Additionally, light sources may output light at a subset of wavelengths from the visible spectrum. For example, a light source may be continuous between approximately 550 nm to 700 mm, a light source may have peaks at approximately 400 nm and 550 nm, and the like. Additionally, wavelengths of radiation other than visible light are contemplated. For example, radiation may include infrared and near infrared sources, ultraviolet sources, electron beam sources, x-ray sources, and the like.

Further embodiments can be envisioned to one of ordinary skill in the art after reading the attached documents. In other embodiments, combinations or sub-combinations of the above disclosed invention can be advantageously made. The block diagrams of the architecture and flow charts are grouped for ease of understanding. However it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A method for profiling film media comprises:
   providing a frame of film media including a plurality of patches including a first patch, and a second patch, wherein the first patch is exposed to a first RGB color combination, and wherein the second patch is exposed to a second RGB color combination;
   providing an illumination source configured to output a beam of light;
   separating the beam of light into a beam of light at approximately a first wavelength and into a beam of light at approximately a second wavelength;
   illuminating the first patch with the beam of light at approximately the first wavelength;
   determining first transmissions from the first patch in response to the beam of light at approximately the first wavelength; thereafter
   substantially simultaneously illuminating the first patch with the beam of light at approximately the second wavelength and illuminating the second patch with the beam of light at approximately the first wavelength;
   substantially simultaneously determining second transmissions from the first patch in response to the beam of light at approximately the second wavelength, and determining first transmissions from the second patch in response to the beam of light at approximately the first wavelength; thereafter
   illuminating the second patch with the beam of light at approximately the second wavelength;
   determining second transmissions from the second patch in response to the beam of light at approximately the second wavelength; thereafter
   determining an XYZ color space representation of the first transmissions and the second transmissions for the first patch; and
   determining an XYZ color space representation of the first transmissions and the second transmissions for the second patch.

2. The method of claim 1
   wherein the beam of light at approximately the first wavelength comprises a beam of light comprising light a range of wavelengths including the first wavelength; and
   wherein the range of wavelengths is less than approximately 5 nanometers.

3. The method of claim 2 wherein the range of wavelengths is approximately 4.5 nanometers or less.

4. The method of claim 1
   wherein separating the beam of light into the beam of light at approximately the first wavelength and into the beam of light at approximately the second wavelength comprises:
   receiving in an optical structure the beam of light; and
   separating in the optical structure the beam of light into the beam of light at approximately the first wavelength and the beam of light at approximately the second wavelength; and
   outputting from the optical structure the beam of light at approximately the first wavelength angularly displaced from the beam of light at approximately the second wavelength;
   wherein the optical structure is selected from the group consisting of: a prism, a diffraction grating.

5. The method of claim 4 wherein after illuminating the first patch with the beam of light at approximately the first wavelength, and before substantially simultaneously illuminating the first patch with the beam of light at approximately the second wavelength and illuminating the second patch with the beam of light at approximately the first wavelength, the method comprises:
   adjusting the relative position of the optical structure to the beam of light such that the beam of light at approximately the first wavelength that is output from the optical structure is displaced from illuminating the first patch to illuminating the second patch.

6. The method of claim 1 wherein separating the beam of light into the beam of light comprises, separating the beam of light into a plurality of beams of light at a plurality of wavelengths including the first wavelength and the second wavelength, wherein the beam of light is continuous between the first wavelength and the second wavelength.

7. The method of claim 1
   wherein the plurality of patches of the frame of film media comprises more than approximately one thousand patches; and
   wherein each patch from the plurality of patches is exposed to a unique RGB color combination.

8. A spectroscope comprises:
   a radiation source configured to provide radiation at a plurality of wavelengths including a first range of wavelengths and a second range of wavelengths;
   a dispersion unit coupled to the radiation source configured to receive the radiation and configured to output the first range of wavelengths angularly displaced from the second range of wavelengths;
   a positioning mechanism coupled to the dispersion unit, wherein the positioning mechanism is configured to position the dispersion unit such that the first range of wavelengths is applied to a first patch of a frame of film but not a second patch of the frame of film at a first time, configured to position the dispersion unit such that the second range of wavelengths is applied to the first patch but not the second patch and the first range of wavelengths is applied to the second patch at a second time, and configured to position the dispersion unit such that the second range of wavelengths is applied to the second patch but not the first patch at a third time; and
   a plurality of detectors comprising a first detector and a second detector, wherein the first detector is configured to detect responses from the frame of film from the first patch, and wherein the second detector is independently configured to detect responses from the frame of film from the second patch.

9. The spectroscope of claim 8 wherein the radiation source is selected from the group consisting of: a visible light source, an infrared source, an electron beam source, an ultraviolet source.

10. The spectroscope of claim 8 wherein the radiation source comprises a light source.

11. The spectroscope of claim 10 a wavelength range for the first range of wavelengths is approximately 5 nm.

12. The spectroscope of claim 10 wherein the responses from the frame of film from the first patch are selected from the group consisting of: transmitted light through the frame of film from the first patch, reflected light from the frame of film from the first patch.

13. The spectroscope of claim 10 wherein the light source comprises light having a continuous wavelength between the first range of wavelengths and the second range of wavelengths.

14. The spectroscope of claim 10 further comprising a computation unit coupled to the plurality of detectors, wherein the computation unit is configured to receive the responses from the frame of film from the first patch and configured to convert the responses into XYZ space, wherein the computation unit is configured to receive the responses from the frame of film from the second patch and convert the responses into XYZ space.

15. A method comprises:
    illuminating each of a plurality of patches on a frame of media with unique portions of a spectrum, wherein a first portion of the spectrum illuminates a first patch, wherein a second portion of the spectrum illuminates a second patch, and wherein each of the plurality of patches on the frame of media are prerecorded with unique RGB values;
    determining a first amount of responses for each of the plurality of patches on the frame of media in response to the unique portions of the spectrum;
    repositioning the spectrum relative to the frame of media;
    illuminating each of the plurality of patches on the frame of media with other unique portions of the spectrum, wherein a second portion of the spectrum illuminates the first patch, and wherein a third portion of the spectrum illuminates the second patch;
    determining a second amount of responses for each of the plurality of patches on the frame of media in response to the other unique portions of the spectrum; and
    determining an RGB to XYZ color space representation associated with the frame of media in response to the first amount of responses, the second amount of responses, and to the unique RGB values.

16. The method of claim 15 wherein the first amount of responses for each of the plurality of patches are selected from the group consisting of: transmissions for each of the plurality of patches, reflections for each of the plurality of patches.

17. The method of claim 15 wherein the spectrum is continuous between the first portion of the spectrum and the second portion of the spectrum.

18. The method of claim 17 wherein the frame of media is selected from the group consisting of: opaque media, translucent media, film media.

19. The method of claim 15 further comprising:
    illuminating a dispersion source with a light source; and
    outputting from the dispersion source the spectrum.

20. The method of claim 19 wherein repositioning the spectrum relative to the frame of media comprises repositioning the dispersion source relative to the light source.

* * * * *